United States Patent
Beckman et al.

[11] Patent Number: 5,957,979
[45] Date of Patent: Sep. 28, 1999

[54] MOBILE BEARING KNEE WITH METAL ON METAL INTERFACE

[75] Inventors: Audrey M. Beckman, Warsaw; Paul D. Schoenle, South Bend; James F. Smith, Goshen, all of Ind.

[73] Assignee: Bristol-Myers Squibb Company, New York, N.Y.

[21] Appl. No.: 08/989,729

[22] Filed: Dec. 12, 1997

[51] Int. Cl.⁶ ............................................. A61F 2/38
[52] U.S. Cl. .............................. 623/20; 623/18; 623/16
[58] Field of Search .................... 623/20, 16, 18

[56] References Cited

U.S. PATENT DOCUMENTS

| | | | |
|---|---|---|---|
| 3,869,731 | 3/1975 | Waugh et al. | 3/1 |
| 3,916,451 | 11/1975 | Ruechel et al. | 3/1.91 |
| 4,136,405 | 1/1979 | Pastrick et al. | 3/1.911 |
| 4,216,549 | 8/1980 | Hillberry et al. | 3/1.911 |
| 4,219,893 | 9/1980 | Noiles | 3/1.911 |
| 4,224,696 | 9/1980 | Murray et al. | 3/1.911 |
| 4,224,697 | 9/1980 | Murray et al. | 3/1.911 |
| 4,257,129 | 3/1981 | Volz | 3/1.911 |
| 4,262,368 | 4/1981 | Lacey | 3/1.911 |
| 4,301,553 | 11/1981 | Noiles | 3/1.911 |
| 4,309,778 | 1/1982 | Buechel et al. | 3/1.911 |
| 4,340,978 | 7/1982 | Buechel et al. | 3/1.911 |
| 4,353,136 | 10/1982 | Polyzoides et al. | 3/1.911 |
| 4,470,158 | 9/1984 | Pappas et al. | 3/1.911 |
| 4,586,933 | 5/1986 | Shoji et al. | 623/20 |
| 4,634,444 | 1/1987 | Noiles | 623/20 |
| 4,711,639 | 12/1987 | Grundei | 623/20 |
| 4,728,332 | 3/1988 | Albrektsson | 623/20 |
| 4,755,185 | 7/1988 | Tarr | 623/18 |
| 4,770,663 | 9/1988 | Hanslik et al. | 623/20 |
| 4,808,185 | 2/1989 | Penenberg et al. | 623/20 |
| 4,838,891 | 6/1989 | Branemark et al. | 623/20 |
| 4,883,488 | 11/1989 | Bloebaum et al. | 623/20 |
| 4,888,021 | 12/1989 | Forte et al. | 623/20 |
| 4,911,721 | 3/1990 | Branemark et al. | 623/20 |
| 4,944,757 | 7/1990 | Martinez et al. | 623/20 |
| 4,950,297 | 8/1990 | Elloy et al. | 623/20 |
| 4,963,152 | 10/1990 | Hofmann et al. | 623/18 |
| 5,011,496 | 4/1991 | Forte et al. | 623/20 |
| 5,047,057 | 9/1991 | Lawes | 623/20 |
| 5,059,216 | 10/1991 | Winters | 623/20 |
| 5,064,437 | 11/1991 | Stock et al. | 623/20 |
| 5,080,675 | 1/1992 | Lawes et al. | 623/20 |
| 5,116,376 | 5/1992 | May | 623/20 |
| 5,133,758 | 7/1992 | Hollister | 623/20 |
| 5,171,283 | 12/1992 | Pappas et al. | 623/20 |
| 5,192,328 | 3/1993 | Winters | 623/20 |
| 5,219,362 | 6/1993 | Tuke et al. | 623/20 |
| 5,226,916 | 7/1993 | Goodfellow et al. | 623/20 |
| 5,271,737 | 12/1993 | Baldwin et al. | 623/20 |
| 5,271,747 | 12/1993 | Wagner et al. | 623/20 |
| 5,282,868 | 2/1994 | Bahler | 623/20 |
| 5,282,870 | 2/1994 | Moser et al. | 623/20 |
| 5,314,481 | 5/1994 | Bianco | 623/20 |
| 5,314,483 | 5/1994 | Wehrli et al. | 623/20 |
| 5,326,361 | 7/1994 | Hollister | 623/20 |
| 5,330,533 | 7/1994 | Walker | 623/20 |
| 5,336,267 | 8/1994 | Kubein-Meesenburg et al. | 623/22 |

(List continued on next page.)

FOREIGN PATENT DOCUMENTS 568756  11/1993  European Pat. Off. ................ 623/20

*Primary Examiner*—Mickey Yu
*Assistant Examiner*—Dinh X. Nguyen
*Attorney, Agent, or Firm*—Todd A. Dawson

[57] ABSTRACT

In the subject invention, the articulating component includes a metal tray and a polyethylene bearing molded or otherwise connected to the metal tray. The distal surface of the metal tray, the surface in contact with the tibial component, is highly polished and is substantially flat. The proximal surface of the tibial component, the surface in contact with the articulating component, is likewise highly polished and substantially flat. In use, the two highly polished flat surfaces provide an environment wherein the articulating surface may freely move relative to the tibial component as the patient's knee joint is flexed and extended during movement.

5 Claims, 3 Drawing Sheets

U.S. PATENT DOCUMENTS

| | | | |
|---|---|---|---|
| 5,344,460 | 9/1994 | Turanyi et al. | 623/20 |
| 5,358,530 | 10/1994 | Hodorek | 623/20 |
| 5,358,531 | 10/1994 | Goodfellow et al. | 623/20 |
| 5,370,701 | 12/1994 | Finn | 623/20 |
| 5,387,240 | 2/1995 | Pottenger et al. | 623/20 |
| 5,395,401 | 3/1995 | Bahler | 623/20 |
| 5,413,604 | 5/1995 | Hodge | 623/20 |
| 5,413,608 | 5/1995 | Keller | 623/20 |
| 5,480,446 | 1/1996 | Goodfellow et al. | 623/20 |
| 5,549,689 | 8/1996 | Epstein et al. | 623/20 |
| 5,556,432 | 9/1996 | Kubein-Meesenburg | 623/20 |
| 5,609,639 | 3/1997 | Walker | 623/20 |
| 5,609,644 | 3/1997 | Ashby et al. | 623/20 |
| 5,702,466 | 12/1997 | Pappas et al. | 623/20 |

MOBILE BEARING KNEE WITH METAL ON METAL INTERFACE

FIELD OF THE INVENTION

This invention relates to a prosthetic knee implant of the type commonly referred to as a mobile bearing knee and has specific relevance to a mobile bearing knee implant having a metal or ceramic backed articulating component which contacts a metal or ceramic tibial component.

SUMMARY OF THE INVENTION

Prosthetic knee implants having a tibial articulating surface which is moveable relative to a fixed tibial tray during flexion and extension of the knee joint are known as mobile bearing knees and will be referred to as such throughout this description. Heretofore, mobile bearing knees primarily consist of a tibial component affixed to the prepared proximal end of a tibia and a bearing component made from polyethylene, typically ultra high molecular weight polyethylene (UHMWPE). Generally, there exists some mechanism or a plurality of mechanisms to restrict or limit the movement of the shiftable articulating component relative to the tibial component during movement of the knee. A femoral component replacing a portion of the distal femur and configured to articulate against the articulating component is also required for a complete prosthetic knee joint; however, for the purpose of this application, the particular design of the femoral component or any detail thereof is considered irrelevant.

In the subject invention, the articulating component includes a metal tray and a polyethylene bearing molded, or otherwise connected, to the metal tray. The distal surface of the metal tray, the surface in contact with the tibial component, is highly polished and is substantially flat. The proximal surface of the tibial component, the surface in contact with the articulating component, is likewise highly polished and substantially flat. In use, the two highly polished flat surfaces provide an environment wherein the articulating surface may freely move relative to the tibial component as the patient's knee joint is flexed and extended during movement. In the preferred embodiment, the tibial component includes a hollow frusto-conical projection which extends into the tibial bone. Further, the metal tray of the articulating component includes a frusto-conical projection configured to extend into the frusto-conical projection of the tibial component. The inner dimension of the projection of the tibial tray is greater than the outer dimension of the projection of the metal tray and may be adjusted during manufacturing such that the metal tray, and thereby the articulating surface, is restricted or limited to a specific range of movement relative to the tibial component.

Alternatively, the metal tray and/or tibial component could be made in whole or in part from an ceramic material as is commonly used in the field of orthopaedics.

Accordingly, it is an object of the invention to provide for a novel mobile bearing knee having an articulating component formed with a metal tray for contact against the tibial component.

Another object of this invention is to provide for a novel mobile bearing knee having an articulating component formed with a metal tray for contact against the tibial component, wherein an articulating surface is connected to the metal tray for contact with a femoral component.

Yet another object of the invention is to provide a novel mobile bearing knee having an articulating component formed with a ceramic tray for contact against the tibial component.

Other objects of the invention will become apparent upon a reading of the following description taken with the accompanying drawings.

DESCRIPTION OF THE PREFERRED EMBODIMENT

Figure 1:
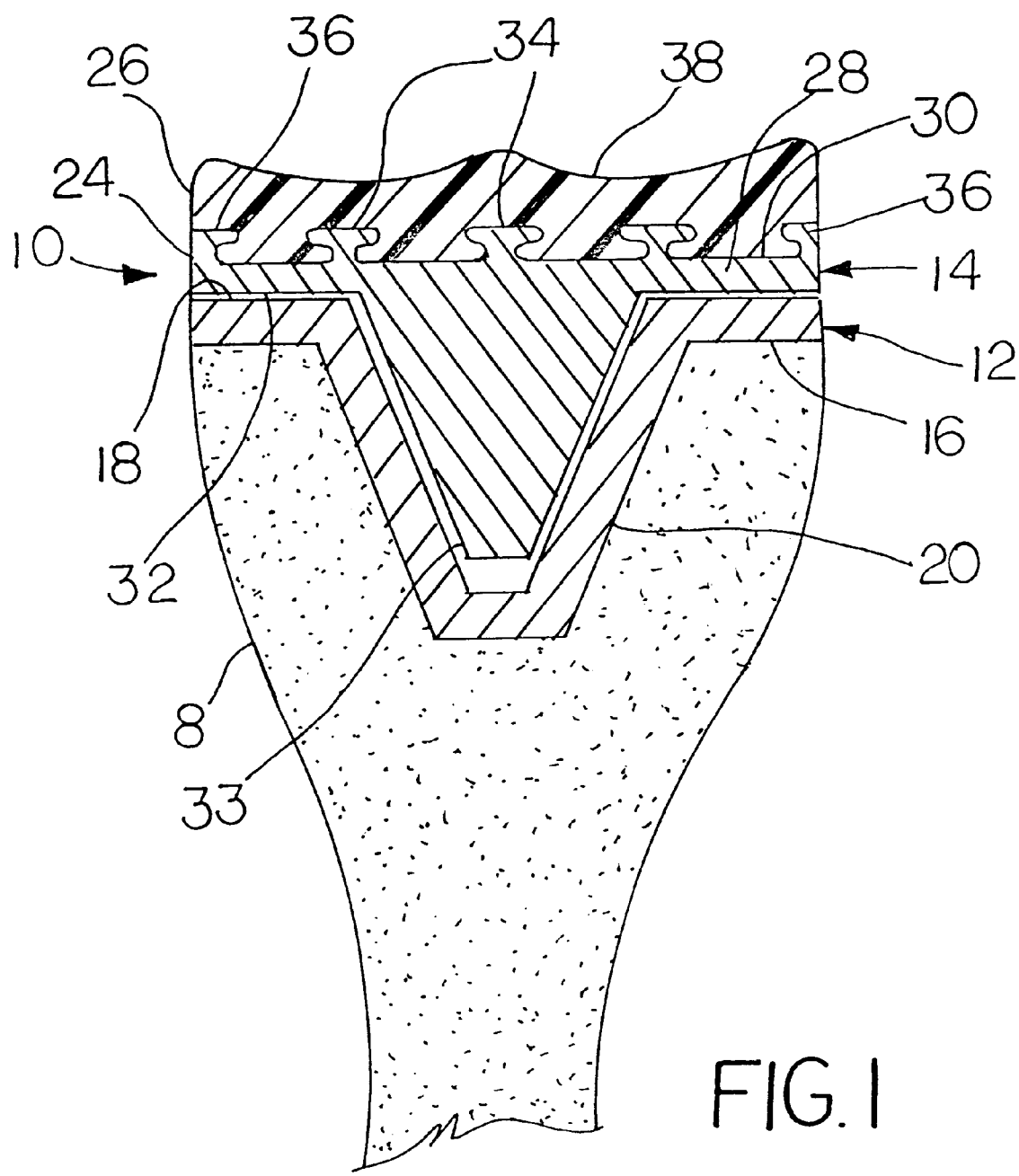
FIG. 1 is a sectional view of the mobile bearing knee of the invention which includes a tibial component and the articulating component and is attached to a proximal end of a prepared tibia.
Figure 2:
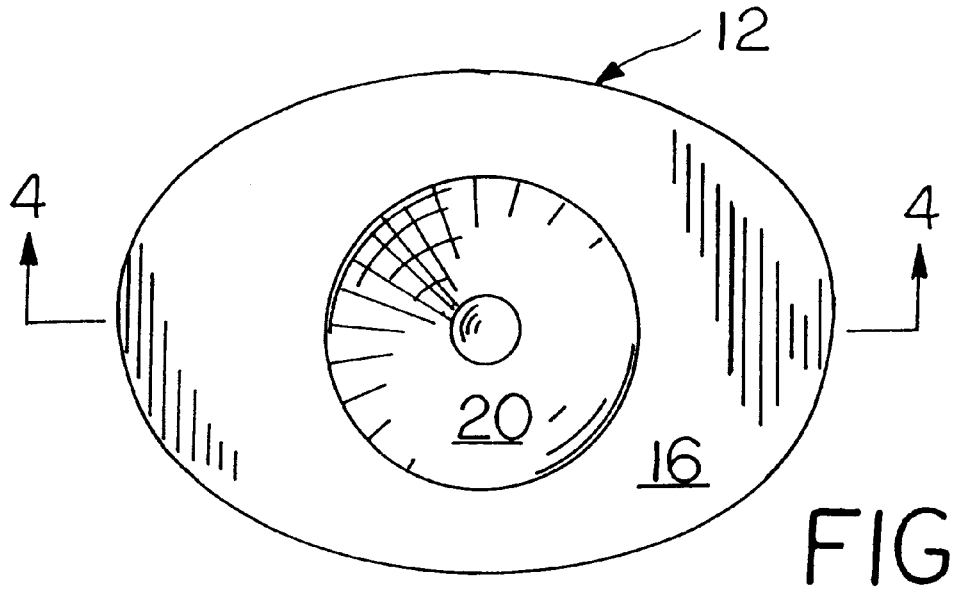
FIG. 2 is a top down view of the tibial component of the mobile bearing knee of the invention.
Figure 3:
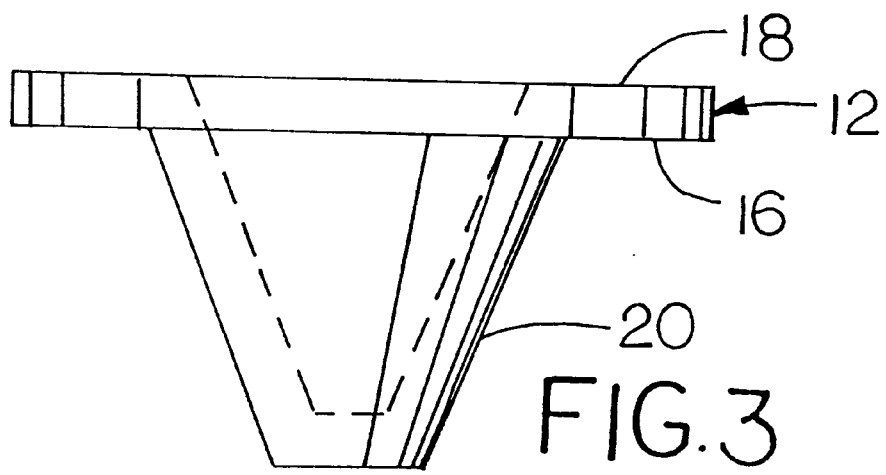
FIG. 3 is a side elevational view of the tibial component of FIG. 2.
Figure 4:
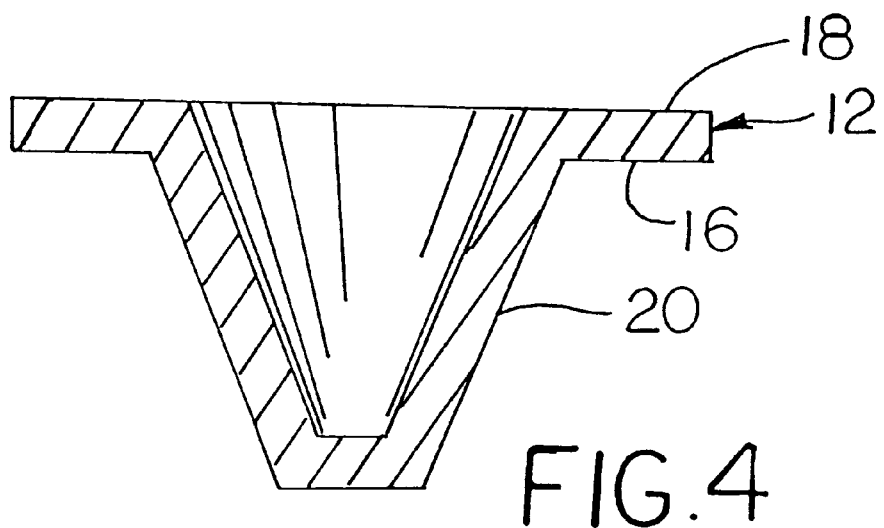
FIG. 4 is a sectional view taken along line 4—4 in FIG. 2.
Figure 5:
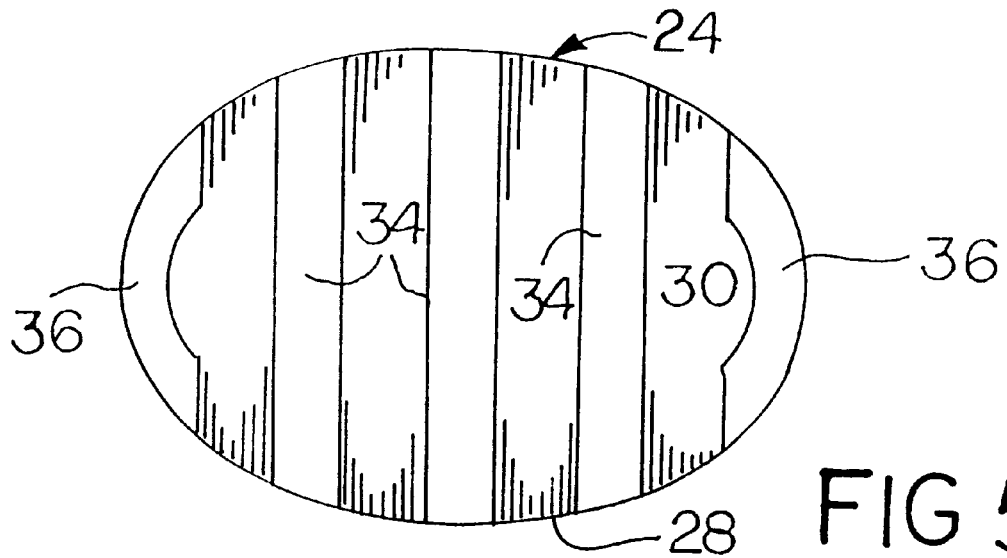
FIG. 5 is a top down view of the metal tray portion of the articulating component of the invention.
Figure 6:
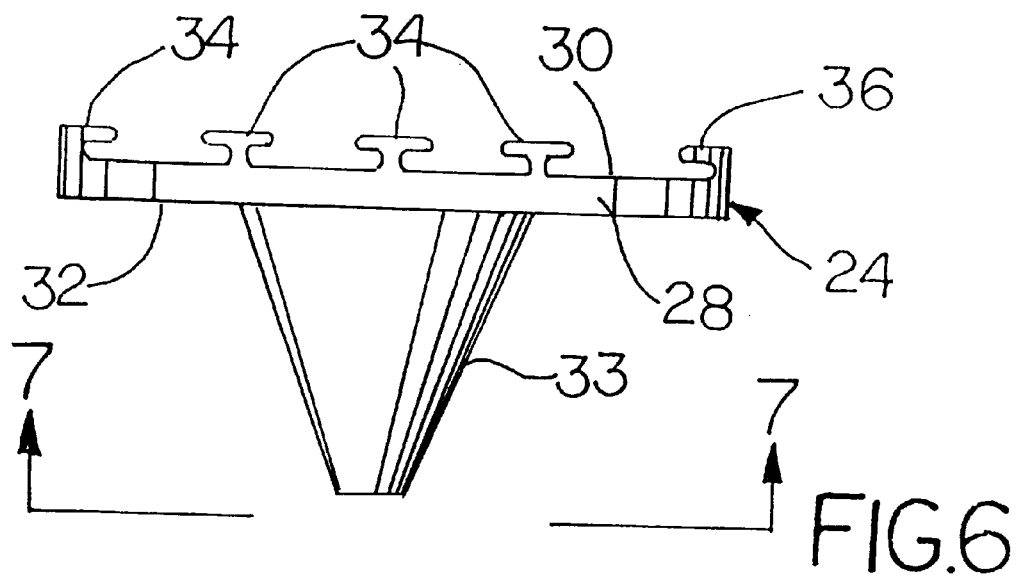
FIG. 6 is a side elevational view thereof.
Figure 7:
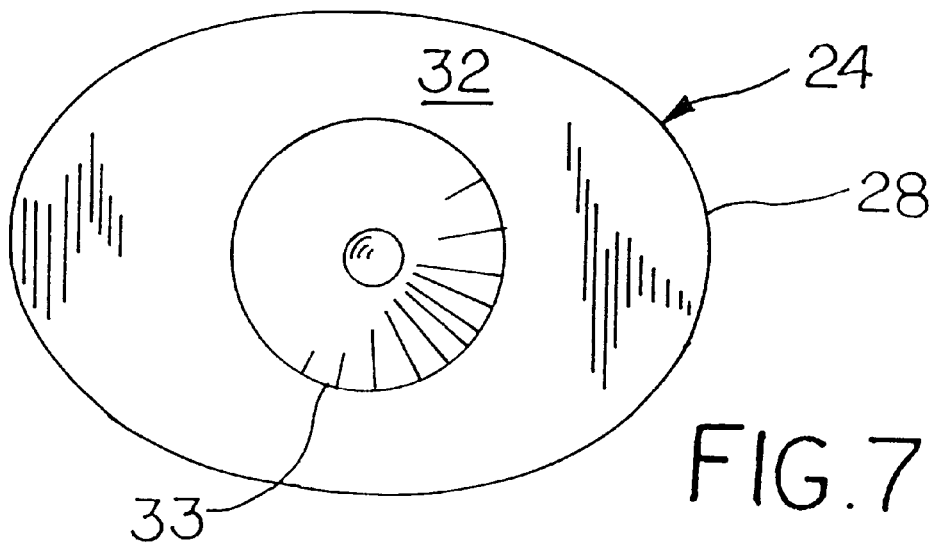
FIG. 7 is a elevational view taken along line 7—7 of FIG. 6.

The preferred embodiments herein described are not intended to be exhaustive or to limit the application to the precise forms disclosed. Rather, they are chosen and described in order to explain the invention to those skilled in the art in order that they may utilize its teachings.

Referring now to the figures, a mobile bearing knee 10 is illustrated in sectional view connected to the proximal end of a prepared tibia 8 (also shown sectioned). Mobile bearing knee 10 includes a tibial component 12 and an articulating component 14.

Tibial component 12 is formed from a known biocompatible metal such as titanium or cobalt-chromium and is configured for contact on its distal face 16 with the tibia 8 and on its proximal face 18 with articulating component 14. The outer periphery of the tibial component is generally ovoid in shape. In the preferred embodiment, the tibial component 12 includes a hollow frusta-conical projection 20 extending from its proximal face 18 through and continuing away from distal face 16. Tibial component 12 is intended to be securely fixed to tibia 8 in a known manner, such as by screws (not shown) or by a layer of bone cement (also not shown) or by a press fit between the bone and tibial component. The particular method of securing the tibial component 12 to the tibia is one of design choice and unimportant to the subject invention. Further, in the preferred embodiment, the proximal face 18 of the tibial component is highly polished and substantially flat.

Articulating component 14 includes a metal tray 24 and a polymer articulating plate 26. The outer periphery of the articulating component 14 is substantially ovoid and is intended to substantially match the outer periphery of the tibial component 12, however, such should not be considered a limitation on the invention. Metal tray 24 is formed from a known bio-compatible metal such as titanium or cobalt-chromium and includes a plate portion 28 having a proximal surface 30 and a distal surface 32. A frusta-conical projection 33 extends away from distal surface 32. In the preferred embodiment, the distal surface of plate portion 28 is highly polished and substantially flat. The proximal surface includes a plurality of rails 34 which, in the preferred embodiment, have a generally T-shaped cross section. A pair of inverted L-shaped side rails 36 extend upwardly from the proximal surface 30 and define the lateral boundaries for the plate. The articulating plate 26 is formed having an articulating surface 38 configured for contact with the condylar portions of a femoral knee implant (not shown) in a known manner. The articulating plate may be molded directly to the metal tray 24 in the manufacturing environment. Alternatively, the proximal surface of the metal tray may be modified in keeping with known methods to allow the articulating plate 26 to be snapped onto the metal tray 24. Whether the articulating plate 26 is molded or snap fitted onto the metal tray 24 is not pertinent to the invention and may be modified within the keeping of the invention by one skilled in the art.

In use, the proximal surface of the tibial is prepared to accept the tibial tray 12 and the tibial tray is connected or otherwise securely fixed to the proximal tibia in a known manner. Next, the articulating component 14 is placed onto the tibial component 12 so the projection 33 from the articulating component 14 resides within the hollow projection 20 of the tibial tray. The outer dimension of projection 33 is slightly smaller than the inner dimension of the projection 20 such that projection 33 is able to move within projection 20 a limited amount. In this manner, the designer of the mobile bearing knee 10 can provide for a proper amount of movement of the articulating component 14 relative to the tibial tray 12. The exact amount of such movement or the difference between the inner dimension of projection 20 and the outer dimension of projection 33, at this point, is one of mere design choice. Since the proximal surface 18 of the tibial component 12 and the distal face 32 of the articulating component 14 are formed from metal and are highly polished and flat, during flexion and extension of the knee joint, the articulating surface may shift relative to the tibial component limited only by the contact between the inner dimension of projection 20 and the outer dimension of projection 33. It is anticipated that natural body fluids near the joint will act as a lubricant between the tibial component and the articulating component.

It should be understood that a wide variety of mechanisms for limiting movement between the articulating component and the tibial component may be developed and the application should not be limited to the precise forms disclosed. For example, the tibial component could include a post extending proximally into the articulating component to serve as a means for limiting the relative movement between the two components. Further, the tibial component, or articulating component, could include a plurality of tabs that could extend either into slots in the other component or be positioned about the periphery and contact the periphery of the other component. Regardless of the particular mechanical means employed to limit movement between the two components, it is important that the proximal surface of the tibial component and the distal surface of the metal tray of the articulating component be substantially flat and highly polished.

It may be desirable to place a quantity of lubricating fluid such as synovial fluid in the gap formed between projection 33 and hollow projection 20 to aid in lubricating the mobile bearing knee and thereby reduce friction.

It should be understood that while the subject invention has been described as being formed from a metal or metal alloy, such should not be considered a limitation to the invention. The tibial component 12 and the tibial tray 14 could be formed from a bio-compatible ceramic material and still be in keeping with the invention.

It should also be understood that the invention is not to be limited to the precise forms disclosed, rather, it may be modified in keeping with the appended claims.

We claim:

1. A mobile bearing knee comprising a metal tibial component having a distal surface and a proximal surface, and an articulating component having a distal surface and a proximal surface, wherein the distal surface of the articulating component is placed in sliding engagement with the proximal surface of the metal tibial component, a limiting means extending between the articulating component and the tibial component for limiting the sliding engagement between the articulating component and the tibial component to a predetermined range wherein the limiting means include a hollow projection extending through the proximal surface and distal surface of the tibial component and away from the distal surface, the limiting means further including a projection extending into the hollow projection of the tibial component, the hollow projection of the tibial component having an inner dimension and the projection of the articulating component having an outer dimension, wherein the inner dimension of the hollow projection is larger than the other dimension of the projection from the articulating component such that the projection from the articulating component is shiftable within the hollow projection with the distal surface of the articulating component in sliding engagement with the proximal surface of the tibial component.

2. The mobile bearing knee of claim 1 wherein the proximal surface of the articulating component is formed from a polyethylene material and is configured for contact with condylar bearing surfaces of a femoral prosthetic implant.

3. The mobile bearing knee of claim 1 wherein the tibial component and the distal surface of the articulating component are formed from a bio-compatible metal.

4. The mobile bearing knee of claim 3 wherein the proximal surface of the tibial component is substantially flat and is highly polished.

5. The mobile bearing knee of claim 1 wherein the distal surface of the articulating component and the proximal surface of the tibial component are formed from a bio-compatible ceramic.

* * * * *